United States Patent [19]

Sauermann et al.

[11] Patent Number: 5,710,177
[45] Date of Patent: Jan. 20, 1998

[54] SYNERGISTIC COMBINATIONS OF ACTIVE SUBSTANCE FOR THE COSMETIC OR DERMATOLOGICAL CARE OF THE SKIN, HAIR & NAILS

[75] Inventors: Gerhard Sauermann, Wiemersdorf; Uwe Schönrock, Norderstedt; Volker Schreiner, Hamburg; Franz Stäb, Echem, all of Germany

[73] Assignee: Beiersdorf AG, Hamburg, Germany

[21] Appl. No.: 448,620

[22] PCT Filed: Dec. 7, 1993

[86] PCT No.: PCT/DE93/01166

§ 371 Date: Aug. 11, 1995

§ 102(e) Date: Aug. 11, 1995

[87] PCT Pub. No.: WO94/14412

PCT Pub. Date: Jul. 7, 1994

[30] Foreign Application Priority Data

Dec. 18, 1992 [DE] Germany .................. 42 42 876.9

[51] Int. Cl.⁶ .................. A61K 31/19; A61K 31/415
[52] U.S. Cl. .................. 514/557; 424/70.1; 424/400; 424/401; 514/387; 514/861; 514/864; 514/880; 514/881
[58] Field of Search .................. 514/557, 387, 514/881, 880, 861, 864; 424/70.1, 400, 401

[56] References Cited

FOREIGN PATENT DOCUMENTS 0383467  8/1990  European Pat. Off. .

Primary Examiner—Shelley A. Dodson
Attorney, Agent, or Firm—Sprung Kramer Schaefer & Briscoe

[57] ABSTRACT

Cosmetic and/or dermatological active compound combinations comprising a) an active amount of biotin and/or biotin esters, b) an active amount of one or more α-hydroxycarboxylic acids of the formula $$R'(R'')(OH)C\ COOH$$

and/or an active amount of one or more α-ketocarboxylic acids of the formula $$R'C(O)\ COOH$$

or their physiologically acceptable salts or esters wherein R' and R" represent H-; branched or unbranched $C_{1-25}$-alkyl- or $C_{1-25}$-alkyl-substituted by one or more carboxyl groups and/or hydroxyl groups and/or a aldehyde groups and/or oxo groups (keto groups); phenyl- or phenyl substituted by one or more carboxyl groups and/or hydroxyl groups and/or branched and/or unbranched $C_{1-25}$-alkyl groups; or wherein the α-carbon atom of the α-hydroxycarboxylic acid, together with R' and R", forms a cycloalkyl group having 3 to 7 ring atoms or the cycloalkyl substituted by one or more carboxyl groups and/or hydroxyl groups and/or oxo groups (keto groups) and/or branched and/or unbranched $C_{1-25}$-alkyl groups; and c) an active amount of one or more antioxidants.

16 Claims, No Drawings

SYNERGISTIC COMBINATIONS OF ACTIVE SUBSTANCE FOR THE COSMETIC OR DERMATOLOGICAL CARE OF THE SKIN, HAIR & NAILS

DESCRIPTION

The present invention relates to cosmetic and/or dermatological active compound combinations for cosmetic and/or dermatological care of the skin and/or of the integumentary appendages, and to cosmetic and/or dermatological formulations comprising such active compound combinations. The invention furthermore relates to methods for care and regeneration of the skin and/or the integumentary appendages and to the use of cosmetic and/or dermatological active compound combinations for cosmetic and/or dermatological care of the skin and/or of the integumentary appendages.

The integumentary appendages include head and body hair and, in particular, the finger nails and toe nails.

Skin care in the context of the invention is primarily to be understood as meaning that the natural function of the skin as a barrier against environmental influences (for example dirt, foreign substances, micro-organisms) and against the loss of endogenous substances (for example water, electrolytes, natural moisture-binding substances) is intensified, assisted and, if necessary, re-established.

If the natural function of the skin is disturbed, increased absorption of toxic and/or allergenic foreign substances or attack by pathogenic microorganisms and, as a consequence, inflammatory or allergic skin reactions may occur.

The human skin constantly loses a certain amount of moisture by endogenous mechanisms, for example by perspiration. However, the skin also loses important functional constituents through external influences, such as daily washing of the body, wind and weather. Although healthy skin is entirely capable of compensating for this loss, the aim of skin care is to assist the skin in compensating for this loss.

However, if the natural regeneration capacity of the skin is inadequate, for example as a result of severe stress or even an illness, it is essential to assist the endogenous regulation mechanisms for re-establishing the barrier function of the skin by means of external agents which can be applied topically.

The health of nails and their external appearance can be impaired considerably by environmental influences, in particular by solvents in many nail varnish removers, but also by frequent contact with other liquid cleaning agents, for example washing-up liquids, detergents and polishes.

Nail care products should clean finger and toe nails and give them an attractive appearance. Specifically, the aim of nail care is to re-establish and promote a normal functional profile of the toe and finger nails.

Nail varnishes in particular, but also special nail care formulations, often based on cosmetic or dermatological emulsions, are used for nail care.

However, most nail care products of the prior art have proved to be inadequate, since the horny layers of the nails can be penetrated by most nail care products only with difficulty, and usually contain no constituents which adequately assist the skin's own lipid metabolism.

It has been found, surprisingly, and therein lies the achievement of the object, that cosmetic and/or dermatological active compound combinations comprising a) an active amount of biotin and/or biotin esters,
b) an active amount of one or more α-hydroxycarboxylic acids of the general formula

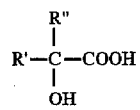

and/or an active amount of one or more α-ketocarboxylic acids of the general formula

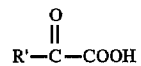

wherein R' and R" in each case independently of one another are chosen from the group consisting of (b1) H-, (b2) branched or unbranched $C_{1-25}$-alkyl-, (b3) branched or unbranched $C_{1-25}$-alkyl- which is substituted by one or more carboxyl groups and/or hydroxyl groups and/or aldehyde groups and/or oxo groups (keto groups), (b4) phenyl- and (b5) phenyl- which is substituted by one or more carboxyl groups and/or hydroxyl groups and/or branched and/or unbranched $C_{1-25}$-alkyl groups, or wherein the α-carbon atom of the α-hydroxycarboxylic acid, together with R' and R", forms an (b6) unsubstituted cycloalkyl group having 3 to 7 ring atoms or a (b7) cycloalkyl group having 3 to 7 ring atoms which is substituted by one or more carboxyl groups and/or hydroxyl groups and/or oxo groups (keto groups) and/or branched and/or unbranched $C_{1-25}$-alkyl groups, and wherein the α-hydroxycarboxylic acid or the α-hydroxycarboxylic acids or the α-ketocarboxylic acid or the α-ketocarboxylic acids can optionally be present in the form of their physiologically tolerated salts and/or ethyl esters and/or methyl esters, and c) if appropriate an active amount of one or more antioxidants, remedy the defects of the prior art.

Biotin (D-cis-hexahydro-2-oxothieno[3,4-d]imidazole-4-valeric acid) is occasionally also called vitamin H (skin vitamin), although it is now counted among the vitamins of the B group (vitamin B7). Nevertheless, in the narrower sense, it is not a vitamin since it can be synthesized by human intestinal flora. However, it is essential as a prosthetic group (also called "coenzyme R" as such) of enzymes which catalyse carboxylations and decarboxylations in the organism (biotin enzymes). Biotin is used therapeutically, for example, for treatment of seborrhoeic dermatitis in infants.

Biotin and its esters are characterized by the following generic chemical structural formula:

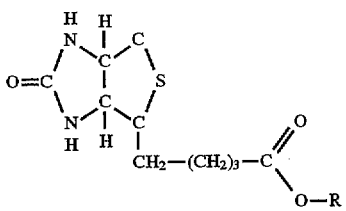

According to the invention, R=H, branched or unbranched $C_{1-18}$-alkyl- or branched or unbranched $C_{1-18}$-alkenyl-. Those structures in which R=H, methyl or ethyl are preferred.

The α-hydroxycarboxylic acids according to the invention are advantageously chosen from the following classes of substance:

(b2) α-hydroxy-fatty acids, these in turn being particularly advantageously chosen from the group consisting of $C_{10-18}$-alkylcarboxylic acids, (b3) α-hydroxy-sugar acids or aliphatic α-hydroxy-fruit acids, (b4) unsubstituted aromatic α-hydroxycarboxylic acids (for example mandelic acid) and (b5) substituted aromatic α-hydroxycarboxylic acids.

The α-hydroxy-fatty acids in section (b2) are particularly advantageously chosen from the group consisting of α-hydroxycarboxylic acids according to the formula

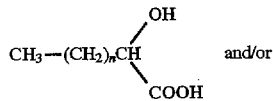

α-hydroxy-isocarboxylic acids according to the formula

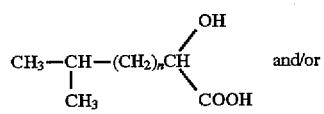

α-hydroxy-anteisocarboxylic acids according to the formula

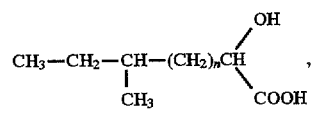

wherein n in each case is a number from 7 to 31.

α-Hydroxycarboxylic acids which are $C_{16}$ substances, that is to say carry a branched or unbranched $C_{14}H_{29}$ chain on the α-carbon atom, are particularly advantageously to be used in the context of the present invention.

It is furthermore advantageous to use mixtures of such aliphatic α-hydroxycarboxylic acids, in particular in the form of wool wax acid mixtures, in which the content of α-hydroxycarboxylic acids is 20–30% by weight, based on the total composition.

The α-hydroxy-sugar acids under point (b3) are particularly advantageously chosen from the group consisting of aldonic acids, for example gluconic acid or galactonic acid, aldaric acids, for example glucaric acid and galactaric acid (and also the fruit acid tartaric acid, which also falls under the definition of aldaric acid)

uronic acids, for example glucuronic acid or galacturonic acid and glyceric acid The aliphatic α-hydroxy-fruit acids under point (b3) are particularly advantageously chosen from the group consisting of malic acid, lactic acid, citric acid and tartaric acid.

Malic acid (hydroxysuccinic acid) is characterized by the following chemical structure:

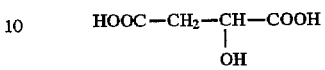

Lactic acid (2-hydroxypropanoic acid) is characterized by the following chemical structure:

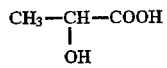

Citric acid(2-hydroxy-1,2,3-propanetricarboxylic acid) is characterized by the following chemical structure:

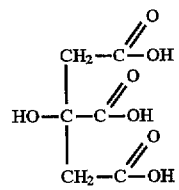

As is known, citric acid is used for buffering cosmetic and/or dermatological formulations, and also as a synergist for antioxidants in skin and hair cosmetics.

Tartaric acid (dihydroxysuccinic acid) is characterized by the following chemical structure:

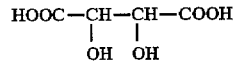

The preferred α-ketocarboxylic acid is pyruvic acid (α-oxopropanoic acid). It is distinguished by the following structure:

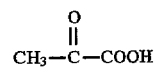

According to the invention, all the antioxidants suitable or customary for cosmetic and/or dermatological uses can be used as antioxidants which are favourable but nevertheless optionally to be used.

The antioxidants are particularly advantageously chosen from the group consisting of ascorbic acid (vitamin C), ascorbic acid derivatives, the various tocopherols (vitamin E) and tocopheryl esters or other tocopherol derivatives, folic acid (formerly called vitamin $B_c$, $B_9$ or M, now assigned to the vitamin $B_2$ group), phytic acid (inositol-hexaphosphoric acid, also fytic acid), the various ubiquinones (mitoquinones, coenzyme Q), bile extract, cis- and/or trans-urocanic acid (4-imidazolylacrylic acid), carnosine (N-β-alanyl-L-histidine, ignotine), histidine, flavones or flavonoids, cystine (3,3'-dithiobis(2-aminopropionic acid)), cysteine (2-amino-3-mercaptopropionic acid) and derivatives thereof (for example N-acetylcysteine), the various carotenes (in particular β-carotene and lycopene (psi-carotene)), tyrosine (2-amino-3-(4-hydroxyphenyl)-propionic acid), α-liponic acid (1,2-dithiolane-3-pentanoic acid), glutathione (gamma-L-glutamyl-L-cysteineglycine) and glutathione esters, as well as zinc oxide and zinc salts (for example $ZnSO_4$).

Those active compound combinations in which the weight ratio of biotin and/or esters thereof to the α-hydroxycarboxylic acid or acids, in particular the α-hydroxy-fruit acid or acids, preferably citric acid, is in the range from 1:500 to 20:1 are particularly advantageous.

Advantageous embodiments of the present invention relate to cosmetic and/or dermatological formulations having a) an active amount of biotin and/or biotin esters, b) an active amount of one or more α-hydroxycarboxylic acids and/or α-ketocarboxylic acids and c) if appropriate an active amount of one or more antioxidants.

Particularly advantageous embodiments of the present invention relate to cosmetic and/or dermatological formulations having a) an active amount of biotin and/or biotin esters, b) an active amount of citric acid and c) if appropriate an active amount of one or more antioxidants.

Preferred formulations are those having a content of 0.001–0.20% by weight of biotin and/or biotin esters, 0.001–5.00% by weight of one or more α-hydroxycarboxylic acids and/or α-ketocarboxylic acids and 0.001–10.00% by weight of an antioxidant or several antioxidants, in each case based on the total weight of the formulations.

Particularly preferred formulations are those having a content of 0.001–0.20% by weight of biotin and/or biotin esters, 0.001–5.00% by weight of citric acid and 0.001–10.00% by weight of an antioxidant or several antioxidants, in each case based on the total weight of the formulations.

If bile extract and/or α-liponic acid is or are the antioxidant or antioxidants, it is advantageous to choose the particular concentrations thereof from the range from 0.001–2.00% by weight, based on the total weight of the formulation.

If vitamin E and/or derivatives thereof is or are used as the antioxidant or antioxidants, it is advantageous to choose the particular concentrations thereof from the range from 0.001–4.00% by weight, based on the total weight of the formulation.

If carotenes and/or derivatives thereof and/or lycopine is or are the antioxidant or antioxidants, it is advantageous to choose the particular concentrations thereof from the range from 0.001–10.00% by weight, based on the total weight of the formulation.

If urocanic acid is the antioxidant or one of the antioxidants, it is advantageous to choose its concentration from the range from 0.001–2.00% by weight, based on the total weight of the formulation.

The invention also relates to the use of cosmetic and/or dermatological active compound combinations of a) an active amount of biotin and/or biotin esters, b) an active amount of one or more α-hydroxycarboxylic acids and/or α-ketocarboxylic acids and c) if appropriate an active amount of one or more antioxidants, or cosmetic and/or dermatological formulations containing such active compound combinations, for care of the skin and/or of the integumentary appendages.

The invention particularly relates to the use of cosmetic and/or dermatological active compound combinations of a) an active amount of biotin and/or biotin esters, b) an active amount of citric acid and c) if appropriate an active amount of one or more antioxidants or cosmetic and/or dermatological formulations comprising such active compound combinations, for care of the skin and/or of the integumentary appendages.

The invention furthermore relates to a method for care of the skin and/or of the integumentary appendages, characterized in that cosmetic active compound combinations comprising a) an active amount of biotin and/or biotin esters, b) an active amount of one or more α-hydroxycarboxylic acids and/or α-ketocarboxylic acids and c) if appropriate an active amount of one or more antioxidants, or cosmetic formulations comprising such active compound combinations, are applied to the skin and/or the integumentary appendages.

The invention particularly relates to a method for care of the skin and/or of the integumentary appendages, characterized in that cosmetic active compound combinations comprising a) an active amount of biotin and/or biotin esters, b) an active amount of citric acid and c) if appropriate an active amount of one or more antioxidants, or cosmetic formulations comprising such active compound combinations, are applied to the skin and/or the integumentary appendages.

It was moreover astonishing that the active compound combinations and cosmetic and/or dermatological formulations according to the invention are capable of improving the appearance of aged skin, which is characterized, above all, by a lack of the skin's own lipids.

It is assumed that the active compound combinations according to the invention stimulate the endogenous capacities for synthesizing skin fats or biochemical precursors thereof and for regulating lipid metabolism in the positive sense.

The invention therefore also relates to the use of cosmetic and/or dermatological active compound combinations of a) an active amount of biotin and/or biotin esters, b) an active amount of one or more α-hydroxycarboxylic acids and/or α-ketocarboxylic acids and c) if appropriate an active-amount of one or more antioxidants, or cosmetic and/or dermatological formulations comprising such active compound combinations, for improving the appearance of dry skin.

The invention particularly relates to the use of cosmetic and/or dermatological active compound combinations of a) an active amount of biotin and/or biotin esters, b) an active amount of citric acid and c) if appropriate an active amount of one or more antioxidants, or cosmetic and/or dermatological formulations comprising such active compound combinations, for improving the appearance of dry skin.

In particular, the active compound combinations according to the invention and cosmetic and/or dermatological formulations comprising such active compound combinations are capable of moderating the appearance of dry skin and of helping patients suffering from this appearance to achieve a more favourable skin fat status. The invention therefore also relates to the use of cosmetic and/or dermatological active compound combinations of a) an active amount of biotin and/or biotin esters, b) an active amount of one or more α-hydroxycarboxylic acids and/or α-ketocarboxylic acids and c) if appropriate an active amount of one or more antioxidants, or to the use of cosmetic and/or dermatological active compound combinations of a) an active amount of biotin and/or biotin esters, b) an active amount of citric acid and c) if appropriate an active amount of one or more antioxidants, or cosmetic and/or dermatological formulations comprising such active compound combinations, for improving the appearance of aged skin.

The invention furthermore relates to the use of cosmetic and/or dermatological active compound combinations of a) an active amount of biotin and/or biotin esters, b) an active amount of one or more α-hydroxycarboxylic acids and/or α-keto-carboxylic acids and c) if appropriate an active amount of one or more antioxidants, or a) an active amount of biotin and/or biotin esters, b) an active amount of citric acid and c) if appropriate an active amount of one or more antioxidants, or cosmetic and/or dermatological formulations comprising such active compound combinations, for stimulating the endogenous capacities for synthesis of skin fats or biochemical precursors thereof.

Finally, it is an advantageous embodiment of the present invention to use the compositions according to the invention, or formulations comprising them, for care of the skin with the clinical picture of atopic dermatitis and/or of seborrhoeic eczema.

It is of course known to the expert that high-quality cosmetic compositions are usually inconceivable without the customary auxiliaries and additives. These include, for example, agents for imparting consistency, fillers, perfume, colouring agents, emulsifiers, additional active compounds, such as vitamins or proteins, light protection agents, stabilizers, antioxidants, insect repellents, alcohol, water, salts, antimicrobially, proteolytically or keratolytically active substances and the like.

The compositions according to the invention can accordingly be used, for example, depending on their composition, as a skin protection cream, cleansing milk, sunscreen lotion, nutrient cream, day or night cream and the like. Where appropriate, it is possible and advantageous to use the compositions according to the invention as a base for pharmaceutical formulations.

The invention also relates to the use of the active compound combinations in skin care cosmetic and/or dermatological formulations.

For use, the cosmetic and dermatological formulations according to the invention are applied to the skin and/or the integumentary appendages in an adequate amount in the manner customary for cosmetics.

Those cosmetic and dermatological formulations which are in the form of a sunscreen composition are particularly favourable. These preferably comprise, in addition to the active compound combinations according to the invention, at least one UVA filter and/or at least one UVB filter and/or at least one inorganic pigment.

Cosmetic and dermatological formulations according to the invention for protection of the skin against UV rays can be in various forms such as, for example, are usually employed for this type of formulation. They can thus be, for example, a solution, an emulsion of the water-in-oil (W/O) type or of the oil-in-water (O/W) type, or a multiple emulsion, for example of the water-in-oil-in-water (W/O/W) type, a gel, a solid stick or else an aerosol.

It is also possible and advantageous in the context of the present invention to incorporate the active compound combinations according to the invention into aqueous systems or surfactant formulations for cleansing the skin and the hair.

The cosmetic and dermatological formulations according to the invention can comprise cosmetic auxiliaries such as are usually used in such formulations, for example preservatives, bactericides, perfumes, substances for preventing foaming, colouring agents, pigments which have a colouring action, thickening agents, surface-active substances, emulsifiers, softening, moistening and/or humectant substances, fats, oils, waxes or other customary constituents of a cosmetic or dermatological formulation, such as alcohols, polyols, polymers, foam stabilizers, electrolytes, organic solvents or silicone derivatives.

If the cosmetic or dermatological formulation is a solution or lotion, solvents which can be used are:

water or aqueous solutions;

oils, such as triglycerides of capric or caprylic acid, but preferably castor oil;

fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids;

alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

Mixtures of the abovementioned solvents are used in particular. Water can be a further constituent of alcoholic substances.

Emulsions according to the invention, for example in the form of a skin protection cream, a skin lotion or a cosmetic milk, for example in the form of a sunscreen cream or a sunscreen milk, are advantageous and comprise, for example, the fats, oils, waxes and other fatty substances mentioned, as well as water and an emulsifier such as is usually used for such a type of formulation.

Gels according to the invention usually comprise alcohols of low C number, for example ethanol, isopropanol, 1,2-propanediol, glycerol and water, or an abovementioned oil in the presence of a thickening agent, which, in the case of oily-alcoholic gels, is preferably silicon dioxide or an aluminium silicate, and in the case of aqueous-alcoholic or alcoholic gels, is preferably a polyacrylate.

Solid sticks according to the invention comprise, for example, naturally occurring or synthetic waxes, fatty alcohols or fatty acid esters. Lipcare sticks are preferred.

Suitable propellants for cosmetic and/or dermatological formulations according to the invention which can be sprayed from aerosol containers are the customary known highly volatile liquefied propellants, for example hydrocarbons (propane, butane, isobutane), which can be employed by themselves or as a mixture with one another. Compressed air is also advantageously to be used.

The expert of course knows that there are propellant gases which are non-toxic per se and which would in principle be suitable for the present invention, but which should nevertheless be avoided because of an unacceptable effect on the environment or other concomitant circumstances, in particular fluorohydrocarbons and fluorochlorohydrocarbons (CFCs).

The cosmetic and/or dermatological formulations for protection of the skin comprise 0.001–0.20% by weight of biotin and/or biotin esters,
0.001–5.00% by weight of one or more $\alpha$-hydroxycarboxylic acids and/or $\alpha$-ketocarboxylic acids, in particular citric acid, and
0.001–10.00% by weight of an antioxidant or several antioxidants, in each case based on the total weight of the formulations.

They can preferably furthermore comprise substances which absorb UV radiation in the UVB range, the total amount of filter substances being, for example, 0.1% by weight to 30% by weight, preferably 0.5 to 10% by weight, in particular 1 to 6% by weight, based on the total weight of the formulations, in order to provide cosmetic and/or dermatological formulations which protect the skin against the entire range of ultraviolet radiation. They can also be used as sunscreen compositions.

The UVB filters can be oil-soluble or water-soluble. Oil-soluble substances which may be mentioned are, for example:

3-benzylidenecamphor derivatives, preferably 3-(4-methylbenzylidene)camphor or 3-benzylidenecamphor;

4-aminobenzoic acid derivatives, preferably 2-ethylhexyl 4-(dimethylamino)-benzoate or amyl 4-(dimethylamino)benzoate;

esters of cinnamic acid, preferably 2-ethylhexyl 4-methoxycinnamate or isopentyl 4-methoxycinnamate;

esters of salicylic acid, preferably 2-ethylhexyl salicylate, 4-isopropylbenzyl salicylate homomenthyl salicylate;

derivatives of benzophenone, preferably 2-hydroxy-4-methoxybenzophenone, 2-hydroxy-4-methoxy-4'-methylbenzophenone or 2,2'-dihydroxy-4-methoxybenzophenone;

esters of benzalmalonic acid, preferably 2-ethylhexyl 4-methoxybenzalmalonate;

2,4,6-trianilino-(p-carbo-2'-ethyl-1'-hexyloxy)-1,3,5-triazine.

Water-soluble substances which are to be mentioned are, for example:

salts of 2-phenylbenzimidazole-5-sulphonic acid, such as its sodium, potassium or its triethanolammonium salt, and the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl)sulphonic acid and their salts.

The list of UVB filters mentioned which can be used in combination with the active compound combinations according to the invention is of course not intended to be limiting.

The invention also relates to the combination of a UVA filter according to the invention with a UVB filter, and to a cosmetic or dermatological formulation according to the invention which also comprises a UVB filter.

It may also be advantageous to combine the active compound combinations according to the invention with UVA filters which are usually contained in cosmetic and/or dermatological formulations. Such substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The invention also relates to those combinations or formulations comprising these combinations. The same amounts of UVA filter substances as have been mentioned for UVB filter substances can be used.

Cosmetic and/or dermatological formulations comprising the active compound combinations according to the invention can also comprise inorganic pigments which are usually used in cosmetics for protection of the skin against UV rays. These are oxides of titanium, zinc, iron, zirconium, silicon, manganese, aluminium or cerium and mixtures thereof, as well as modifications in which the oxides are the active agents. The pigments are particularly preferably those based on titanium dioxide. The amounts mentioned for the above combinations can be used.

Cosmetic and dermatological formulations according to the invention for use on the hair are, for example, shampooing agents, formulations which are used for rinsing the hair before or after shampooing, before or after permanent wave treatment or before or after colouring or bleaching the hair, formulations for blow-drying or setting the hair, formulations for colouring or bleaching, a styling and treatment lotion, a hair lacquer or permanent wave compositions. The cosmetic and/or dermatological formulations comprise, if appropriate, additional active compounds, auxiliaries and/or additives such as are usually used in this type of formulation for hair care and hair treatment. Auxiliaries which are used are preservatives, surface-active substances, substances for preventing foaming, emulsifiers, thickening agents, fats, oils, waxes, organic solvents, bactericides, perfumes, colouring agents or pigments, the task of which is to colour the hair or the cosmetic or dermatological formulation itself, electrolytes and additional substances regreasing the hair or scalp.

Cosmetic formulations which are a skin cleansing composition or shampooing composition preferably comprise at least one anionic, non-ionic or amphoteric surface-active substance, or else a mixture of such substances, an active amount of active compound combinations according to the invention and auxiliaries, such as are usually used for this purpose. The surface-active substance or the mixtures of these substances can be present in the shampooing composition in a concentration of between 1% by weight and 50% by weight.

If the cosmetic or dermatological formulations are in the form of a lotion which is rinsed out and is used, for example, before or after bleaching, before or after shampooing, between two shampooing steps or before or after permanent wave treatment, the formulations are, for example, aqueous or aqueous-alcoholic solutions, which comprise surface-active substances if appropriate, preferably non-ionic or cationic surface-active substances, the concentration of which can be between 0.1 and 10% by weight, preferably between 0.2 and 5% by weight. These cosmetic and/or dermatological formulations can also be aerosols with the auxiliaries usually used for this purpose.

A cosmetic formulation in the form of a lotion which is not rinsed out, in particular a lotion for setting the hair, a lotion used for blow-drying the hair or a styling and treatment lotion, is in general an aqueous, alcoholic or aqueous-alcoholic solution and comprises at least one cationic, anionic, non-ionic or amphoteric polymer, or else mixtures thereof, as well as the active compound combinations according to the invention. The amount of polymers used is, for example, between 0.1 and 10% by weight, preferably between 0.1 and 3% by weight.

Cosmetic formulations according to the invention for treatment and care of the hair which comprise active compound combinations according to the invention can be in the form of emulsions which are of the non-ionic or anionic type. Non-ionic emulsions comprise, in addition to water, oils or fatty alcohols which can also be polyethoxylated or polypropoxylated, for example, or also mixtures of the two organic components. If appropriate, these emulsions comprise cationic or surface-active substances.

Cosmetic formulations for treatment and care of the hair can be in the form of gels which, in addition to an active content of the active compound combinations according to the invention and the solvents usually used for this purpose, preferably water, also comprise organic thickening agents, for example gum arabic, xanthan gum, sodium alginate, cellulose derivatives, preferably methylcellulose, hydroxymethylcellulose, hydroxyethylcellulose, hydroxypropylcellulose or hydroxypropylmethylcellulose, or inorganic thickening agents, for example aluminium silicates, such as, for example, bentonites, or a mixture of polyethylene glycol and polyethylene glycol stearate or distearate. The gel comprises the thickening agent, for example, in an amount of between 0.1 and 30% by weight, preferably between 0.5 and 15% by weight.

The amount of active compound combinations according to the invention is preferably chosen such that the corresponding formulations for treatment and care of the hair comprise 0.001–0.20% by weight of biotin and/or biotin esters, 0.001–5.00% by weight of one or more α-hydroxycarboxylic acids and/or α-ketocarboxylic acids, in particular citric acid, and 0.00–10.00% by weight of an antioxidant or several antioxidants, in each case based on the total weight of the formulations.

Cosmetic and dermatological formulations according to the invention for care and re-establishment of toe and finger nails can be in various forms such as, for example, are usually employed in this type of formulation.

They can thus be, for example, a solution, an emulsion of the water-in-oil (W/O) type or of the oil-in-water (O/W) type, or a multiple emulsion, for example of the water-in-oil-in-water (W/O/W) type, a gel, a solid stick or else an aerosol.

These formulations are particularly preferably in the form of emulsions.

The cosmetic and dermatological formulations according to the invention can comprise cosmetic auxiliaries such as are usually used in such formulations, for example preservatives, bactericides, perfumes, substances for preventing foaming, colouring agents, pigments which have a colouring action, thickening agents, surface-active substances, emulsifiers, softening, moistening and/or humectant substances, fats, oils, waxes or other customary constituents of a cosmetic or dermatological formulation, such as alcohols, polyols, polymers, foam stabilizers, electrolytes, organic solvents or silicone derivatives.

If the cosmetic and/or dermatological formulation for care or re-establishment of nails is a solution or lotion, solvents which can be used are:

water or aqueous solutions;

oils, such as triglycerides of capric or caprylic acid, but preferably castor oil;

fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids;

alcohols, diols or polyols of low C number, as well as ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

Mixtures of the abovementioned solvents are used in particular. In the case of alcoholic solvents, water can be a further constituent.

Emulsions according to the invention for nail care comprise, for example, the fats, oils, waxes and other fatty substances mentioned, as well as water and an emulsifier such as is usually used for such a type of formulation.

Gels according to the invention for care and/or re-establishment of nails usually comprise alcohols of low C number, for example ethanol, isopropanol, 1,2-propanediol, glycerol and water, or an abovementioned oil in the presence of a thickening agent, which, in the case of oily-alcoholic gels, is preferably silicon dioxide or an aluminium silicate, and in the case of aqueous-alcoholic or alcoholic gels, is preferably a polyacrylate.

It is however also possible, and where appropriate advantageous, for the active compound combinations according to the invention to be employed in nail varnishes, nail varnish removers, nail hardeners or cuticle removers.

Nail varnishes according to the invention can comprise film-forming agents, resins, solvents and also auxiliaries and additives.

Nail hardeners can comprise substances which crosslink the amino groups of nail keratin.

Cuticle removers can comprise active compounds which soften the cuticle in order to facilitate removal thereof.

The customary requirements imposed by the expert on such formulations and their contents otherwise apply to this group of cosmetic and/or dermatological formulations.

The amount of active compound combinations according to the invention is preferably chosen such that the corresponding cosmetic and/or dermatological formulations for treatment and care of the finger and toe nails comprise 0.001–0.20% by weight of biotin and/or other biotin esters, 0.001–5.00% by weight of one or more α-hydroxycarboxylic acids and/or α-keto-carboxylic acids, in particular citric acid, and 0.001–10.00% by weight of an antioxidant or several antioxidants, in each case based on the total weight of the formulations.

The invention also relates to the process for the preparation of the cosmetic and/or dermatological formulations according to the invention, which is characterized in that biotin and/or biotin esters, preferably in an amount corresponding to 0.001–0.20% by weight, one or more α-hydroxycarboxylic acids and/or α-keto-carboxylic acids, in particular citric acid, preferably in an amount corresponding to 0.001–5.00% by weight, and an antioxidant or several antioxidants, preferably in an amount corresponding to 0.001–5.00% by weight, in each case based on the total weight of the formulations, are incorporated into cosmetic and/or dermatological formulations in a manner known per se.

The following examples are intended to illustrate the present invention without limiting it. Unless stated otherwise, all the amounts, contents and percentages are based on the weight and the total quantity or on the total weight of the formulations.

EXAMPLE 1

| Body lotion I | % by weight |
| --- | --- |
| A: PEG 5 stearyl stearate ("Arlatone 985", ICI) | 4.00 |
| Steareth-20 ("Brij 78", ICI) | 2.00 |
| Capric acid/caprylic acid triglyceride ("Miglyol 812" Dynamit Nobel) | 5.00 |
| Paraffin oil DAB 9 | 5.00 |
| B: Perfume | q.s. |
| Biotin ("D-Biotin", Hoffmann-La Roche) | 0.05 |
| C: Propylene glycol | 5.00 |
| Citric acid | 0.50 |
| Preservative | q.s. |
| Water, completely desalinated | to 100.00 |

The constituents of phases A and C are in each case mixed together, the two phases are combined at 75° C. and the mixture is emulsified. The emulsified mixture of A and C is cooled to 35° C. and combined with phase B, which has likewise been heated to 35° C., and the mixture is stirred until cold.

EXAMPLE 2

| Hair treatment rinse I | % by weight |
| --- | --- |
| Cetyl alcohol | 5.00 |
| Paraffin oil DAB 9 | 3.00 |
| Cocoamidopropylbetaine ("Tego Betain L7", Th.Goldschmidt) | 5.00 |
| Cetimonium chloride ("Dehyquart A", Henkel KGaA) | 5.00 |
| Citric acid as required for pH 4.5–5.5 | |
| Biotin ("D-Biotin", Hoffmann-La Roche) | 0.05 |
| Preservative | q.s. |
| Perfume | q.s. |
| Water, completely desalinated | to 100.00 |

The raw materials are combined, while stirring, and the pH is brought to 4.5–5.5 with the aid of citric acid.

EXAMPLE 3

| Hand protection cream I | % by weight |
| --- | --- |
| A: Polyglycerol 2-sesquiisostearate + beeswax + mineral oil + magnesium stearate ("Hostacerin W/O", Hoechst AG) | 10.00 |
| Ceresin ("Lunacera M", Fuller) | 1.00 |
| Dimethicone ("Silicone Oil AK 100", Wacker) | 2.00 |
| Vaseline DAB 9 | 5.00 |
| Paraffin oil DAB 9 | 7.00 |
| B: Perfume | q.s. |
| Biotin ("D-Biotin", Hoffmann-La Roche) | 0.05 |
| C: Glycerol | 3.00 |
| Citric acid | 0.50 |
| Preservative | q.s. |
| Water, completely desalinated | to 100.00 |

The constituents of phases A and C are in each case mixed together, the two phases are combined at 75° C. and the mixture is emulsified. The emulsified mixture of A and C is cooled to 40° C. and combined with phase B, which has likewise been heated to 40° C., and the mixture is stirred until cold.

EXAMPLE 4

| Night cream (for dry skin) I | % by weight |
| --- | --- |
| A: Mineral oil + wool wax alcohol + octyldodecanol ("Amerchol L500", Amerchol) | 2.50 |
| Laneth-16 + Ceteth-16 + Oleth-16 + Steareth-16 ("Solulan 16", Amerchol) | 2.50 |
| Cetearyl alcohol ("Lanette O", Henkel KGaA) | 5.00 |
| Paraffin oil DAB 9 | 30.00 |
| Microcrystalline wax ("Lunacera MWN", Fuller) | 5.00 |
| B: Perfume | q.s. |
| Biotin ("D-Biotin", Hoffmann-La Roche) | 0.20 |
| C: Methylgluceth-20 ("Glucam E20", Amerchol) | 4.00 |
| Carbomer ("Carbopol 954", B.F. Goodrich) | 0.50 |
| NaOH (20% strength) | q.s. |
| Preservative | q.s. |
| Citric acid | 0.20 |
| Water, completely desalinated | to 100.00 |

Phase A is heated to 75° C. Phase C is prepared by first dispersing the carbomer in water, subsequently adding the other constituents and then heating the mixture to 75° C. Phases A and C are then combined with one another and the mixture is emulsified. NaOH is added to the emulsified mixture of A and C as required and thereafter the mixture is cooled to 40° C. and combined with phase B, which has likewise been heated to 40° C., and the mixture is stirred until cold.

EXAMPLE 5

| Body lotion II | % by weight |
| --- | --- |
| A: PEG 5 stearyl stearate ("Arlatone 985", ICI) | 4.00 |
| Steareth-20 ("Brij 78", ICI) | 2.00 |
| Capric acid/caprylic acid triglyceride ("Miglyol 812" Dynamit Nobel) | 5.00 |
| Butylated hydroxytoluene | 0.05 |
| Paraffin oil DAB 9 | 5.00 |
| B: Perfume | q.s |
| Biotin | 0.05 |

-continued

| Body lotion II | % by weight |
|---|---|
| ("D-Biotin", Hoffmann-La Roche) | |
| C: Propylene glycol | 5.00 |
| Citric acid | 0.50 |
| Preservative | q.s. |
| Water, completely desalinated | to 100.00 |

The constituents of phases A and C are in each case mixed together, the two phases are combined at 75° C. and the mixture is emulsified. The emulsified mixture of A and C is cooled to 35° C. and combined with phase B, which has likewise been heated to 35° C., and the mixture is stirred until cold.

EXAMPLE 6

| Hair treatment rinse II | % by weight |
|---|---|
| Cetyl alcohol | 5.00 |
| Paraffin oil DAB 9 | 3.00 |
| Cocoamidopropylbetaine | 5.00 |
| ("Tego Betain L7", Th.Goldschmidt) | |
| Cetimonium chloride | 5.00 |
| ("Dehyquart A", Henkel KGaA) | |
| Citric acid as required for pH 4.5–5.5 | |
| Biotin | 0.05 |
| ("D-Biotin", Hoffmann-La Roche) | |
| Butylated hydroxytoluene | 0.05 |
| Preservative | q.s |
| Perfume | q.s. |
| Water, completely desalinated | to 100.00 |

The raw materials are combined, while stirring, and the pH is brought to 4.5–5.5 with the aid of citric acid.

EXAMPLE 7

| Hand protection cream II | % by weight |
|---|---|
| A: Polyglycerol 2-sesquiisostearate + beeswax + mineral oil + magnesium stearate ("Hostacerin W/O", Hoechst AG) | 10.00 |
| Ceresin | 1.00 |
| ("Lunacera M", Fuller) | |
| Dimethicone | 2.00 |
| ("Silicone Oil AK 100", Wacker) | |
| Butylated hydroxytoluene | 0.05 |
| Vaseline DAB 9 | 5.00 |
| Paraffin oil DAB 9 | 7.00 |
| B: Perfume | q.s. |
| Biotin | 0.05 |
| ("D-Biotin", Hoffmann-La Roche) | |
| C: Glycerol | 3.00 |
| Citric acid | 0.50 |
| Preservative | q.s. |
| Water, completely desalinated | to 100.00 |

The constituents of phases A and C are in each case mixed together, the two phases are combined at 75° C. and the mixture is emulsified. The emulsified mixture of A and C is cooled to 40° C. and combined with phase B, which has likewise been heated to 40° C. and the mixture is stirred until cold.

EXAMPLE 8

| Night cream (for dry skin) II | % by weight |
|---|---|
| A: Mineral oil + wool wax alcohol + octyldodecanol ("Amerchol L500", Amerchol) | 2.50 |
| Laneth-16 + Ceteth-16 + Oleth-16 + Steareth-16 ("Solulan 16", Amerchol) | 2.50 |
| Cetearyl alcohol | 5.00 |
| ("Lanette O", Henkel KGaA) | |
| Butylated hydroxytoluene | 0.05 |
| Paraffin oil DAB 9 | 30.00 |
| Microcrystalline wax | 5.00 |
| ("Lunacera MWN", Fuller) | |
| B: Perfume | q.s. |
| Biotin | 0.20 |
| ("D-Biotin", Hoffmann-La Roche) | |
| C: Methylgluceth-20 | 4.00 |
| ("Glucam E20", Amerchol) | |
| Carbomer | 0.50 |
| ("Carbopol 954", B.F. Goodrich) | |
| NaOH (20% strength) | q.s. |
| Preservative | q.s. |
| Citric acid | 2.00 |
| Water, completely desalinated | to 100.00 |

Phase A is heated to 75° C. Phase C is prepared by first dispersing the carbomer in water, subsequently adding the other constituents and then heating the mixture to 75° C. Phases A and C are then combined with one another and the mixture is emulsified. NaOH is added to the emulsified mixture of A and C as required and thereafter the mixture is cooled to 40° C. and combined with phase B, which has likewise been heated to 40° C., and the mixture is stirred until cold.

EXAMPLE 9

| Body lotion III | % by weight |
|---|---|
| A: PEG 5 stearyl stearate | 4.00 |
| ("Arlatone 985", ICI) | |
| Steareth-20 | 2.00 |
| ("Brij 78", ICI) | |
| Capric acid/caprylic acid triglyceride | 5.00 |
| ("Miglyol 812" Dynamit Nobel) | |
| Paraffin oil DAB 9 | 5.00 |
| Tocopheryl acetate | 1.00 |
| B: Perfume | q.s. |
| Biotin | 0.05 |
| ("D-Biotin", Hoffmann-La Roche) | |
| C: Propylene glycol | 5.00 |
| Citric acid | 0.50 |
| Preservative | q.s. |
| Water, completely desalinated | to 100.00 |

The constituents of phases A and C are in each case mixed together, the two phases are combined at 75° C. and the mixture is emulsified. The emulsified mixture of A and C is cooled to 35° C. and combined with phase B, which has likewise been heated to 35° C., and the mixture is stirred until cold.

EXAMPLE 10

| Hair treatment rinse III | % by weight |
|---|---|
| Cetyl alcohol | 5.00 |
| Paraffin oil DAB 9 | 3.00 |
| Cocoamidopropylbetaine ("Tego Betain L7", Th.Goldschmidt) | 5.00 |
| Cetimonium chloride ("Dehyquart A", Henkel KGaA) | 5.00 |
| Citric acid as required for pH 4.5–5.5 | |
| Biotin ("D-Biotin", Hoffmann-La Roche) | 0.05 |
| Bile extract | 0.50 |
| Preservative | q.s. |
| Perfume | q.s. |
| Water, completely desalinated | to 100.00 |

The raw materials are combined, while stirring, and the pH is brought to 4.5–5.5 with the aid of citric acid.

EXAMPLE 11

| Hand protection cream III | | % by weight |
|---|---|---|
| A: | Polyglycerol 2-sesquiisostearate + beeswax + mineral oil + magnesium stearate ("Hostacerin W/O", Hoechst AG) | 10.00 |
| | Ceresin ("Lunacera M", Fuller) | 1.00 |
| | Dimethicone ("Silicone Oil AK 100", Wacker) | 2.00 |
| | α-Liponic acid | 0.50 |
| | Vaseline DAB 9 | 5.00 |
| | Paraffin oil DAB 9 | 7.00 |
| B: | Perfume | q.s. |
| | Biotin ("D-Biotin", Hoffmann-La Roche) | 0.05 |
| C: | Glycerol | 3.00 |
| | Citric acid | 0.50 |
| | Preservative | q.s. |
| | Water, completely desalinated | to 100.00 |

The constituents of phases A and C are in each case mixed together, the two phases are combined at 75° C. and the mixture is emulsified. The emulsified mixture of A and C is cooled to 40° C. and combined with phase B, which has likewise been heated to 40° C., and the mixture is stirred until cold.

EXAMPLE 12

| Night cream (for dry skin) III | | % by weight |
|---|---|---|
| A: | Mineral oil + wool wax alcohol + octyldodecanol ("Amerchol L500", Amerchol) | 2.50 |
| | Laneth-16 + Ceteth-16 + Oleth-16 + Steareth-16 ("Solulan 16", Amerchol) | 2.50 |
| | Cetearyl alcohol ("Lanette O", Henkel KGaA) | 5.00 |
| | β-Carotene | 5.00 |
| | Paraffin oil DAB 9 | 30.00 |
| | Microcrystalline wax ("Lunacera MWN", Fuller) | 5.00 |
| B: | Perfume | q.s. |
| | Biotin ("D-Biotin", Hoffmann-La Roche) | 0.20 |
| C: | Methylgluceth-20 | 4.00 |

-continued

| Night cream (for dry skin) III | % by weight |
|---|---|
| ("Glucam E20", Amerchol) | |
| Carbomer ("Carbopol 954", B.F. Goodrich) | 0.50 |
| NaOH (20% strength) | q.s. |
| Preservative | q.s. |
| Citric acid | 0.20 |
| Water, completely desalinated | to 100.00 |

Phase A is heated to 75° C. Phase C is prepared by first dispersing the carbomer in water, subsequently adding the other constituents and then heating the mixture to 75° C. Phases A and C are then combined with one another and the mixture is emulsified. NaOH is added to the emulsified mixture of A and C as required and thereafter the mixture is cooled to 40° C. and combined with phase B, which has likewise been heated to 40° C., and the mixture is stirred until cold.

EXAMPLE 13

| Body lotion IV | | % by weight |
|---|---|---|
| A: | PEG 5 stearyl stearate ("Arlatone 985", ICI) | 4.00 |
| | Steareth-20 ("Brij 78", ICI) | 2.00 |
| | Capric acid/caprylic acid triglyceride ("Miglyol 812" Dynamit Nobel) | 5.00 |
| | Paraffin oil DAB 9 | 5.00 |
| B: | Perfume | q.s. |
| | Biotin ("D-Biotin", Hoffmann-La Roche) | 0.05 |
| C: | Propylene glycol | 5.00 |
| | Lactic acid | 0.50 |
| | Sodium lactate | 1.10 |
| | Preservative | q.s. |
| | Water, completely desalinated | to 100.00 |

The constituents of phases A and C are in each case mixed together, the two phases are combined at 75° C. and the mixture is emulsified. The emulsified mixture of A and C is cooled to 35° C. and combined with phase B, which has likewise been heated to 35° C., and the mixture is stirred until cold.

EXAMPLE 14

| Hair treatment rinse IV | % by weight |
|---|---|
| Cetyl alcohol | 5.00 |
| Paraffin oil DAB 9 | 3.00 |
| Cocoamidopropylbetaine ("Tego Betain L7", Th.Goldschmidt) | 5.00 |
| Cetimonium chloride ("Dehyquart A", Henkel KGaA) | 5.00 |
| Citric acid as required for pH 4.5–5.5 | |
| Biotin ("D-Biotin", Hoffmann-La Roche) | 0.05 |
| Urocanic acid | 1.00 |
| Preservative | q.s. |
| Perfume | q.s. |
| Water, completely desalinated | to 100.00 |

The raw materials are combined, while stirring, and the pH is brought to 4.5–5.5 with the aid of citric acid.

EXAMPLE 15

| Hand protection cream IV | % by weight |
|---|---|
| A: Polyglycerol 2-sesquiisostearate + beeswax + mineral oil + magnesium stearate ("Hostacerin W/O", Hoechst AG) | 10.00 |
| Ceresin ("Lunacera M", Fuller) | 1.00 |
| Dimethicone ("Silicone Oil AK 100", Wacker) | 2.00 |
| Vaseline DAB 9 | 5.00 |
| Paraffin oil DAB 9 | 7.00 |
| B: Perfume | q.s. |
| Biotin ("D-Biotin", Hoffmann-La Roche) | 0.05 |
| C: Glycerol | 3.00 |
| Pyruvic acid | 0.20 |
| NaOH (to pH 4.5–5.5 as required) | |
| Preservative | q.s. |
| Water, completely desalinated | to 100.00 |

The constituents of phases A and C are in each case mixed together, the two phases are combined at 75° C. and the mixture is emulsified. The emulsified mixture of A and C is cooled to 40° C. and combined with phase B, which has likewise been heated to 40° C., and the mixture is stirred until cold.

EXAMPLE 16

| Night cream (for dry skin) III | % by weight |
|---|---|
| A: Mineral oil + wool wax alcohol + octyldodecanol ("Amerchol L500", Amerchol) | 2.50 |
| Laneth-16 + Ceteth-16 + Oleth-16 + Steareth-16 ("Solulan 16", Amerchol) | 2.50 |
| Cetearyl alcohol ("Lanette O", Henkel KGaA) | 5.00 |
| Paraffin oil DAB 9 | 30.00 |
| Microcrystalline wax ("Lunacera MWN", Fuller) | 5.00 |
| Perfume | q.s. |
| Biotin ("D-Biotin", Hoffmann-La Roche) | 0.20 |
| C: Methylgluceth-20 ("Glucam E20", Amerchol) | 4.00 |
| Carbomer ("Carbopol 954", B.F. Goodrich) | 0.50 |
| NaOH (20% strength) | q.s. |
| Preservative | q.s. |
| Glucuronic acid | 0.20 |
| Water, completely desalinated | to 100.00 |

Phase A is heated to 75° C. Phase C is prepared by first dispersing the carbomer in water, subsequently adding the other constituents and then heating the mixture to 75° C. Phases A and C are then combined with one another and the mixture is emulsified. NaOH is added to the emulsified mixture of A and C as required and thereafter the mixture is cooled to 40° C. and combined with phase B, which has likewise been heated to 40° C., and the mixture is stirred until cold.

EXAMPLE 17

| Body care cream | % by weight |
|---|---|
| A: Polyglyceryl 2-sesquiisostearate + beeswax + mineral oil + magnesium stearate + aluminium stearate ("Hostacerin WO", Hoechst) | 3.00 |
| PEG 7-hydrogenated castor oil ("Cremophor WO 7", BASF) | 3.00 |
| Vaseline, white | 15.00 |
| Beeswax ("Permulgin 1550") | 2.00 |
| Microcrystalline wax ("Lunacera M") | 2.00 |
| Aluminium stearate | 0.50 |
| Magnesium stearate | 0.50 |
| B: Perfume | q.s. |
| C: NaOH (to pH 4.5–5.5 as required) | |
| Preservative | q.s. |
| Maleic acid | 0.30 |
| Water, completely desalinated | to 100.00 |

Phase A is heated to 75° C. Phase C is prepared by first dispersing the carbomer in water, subsequently adding the other constituents and then heating the mixture to 75° C. Phases A and C are then combined with one another and the mixture is emulsified. NaOH is added to the emulsified mixture of A and C as required and the mixture is then cooled to 40° C., combined with phase B, which has likewise been heated to 40° C. and stirred until cold.

We claim:

1. Cosmetic and/or dermatologically active compound combinations comprising
   a) an active amount of biotin and/or biotin esters,
   b) an active amount of one or more α-hydroxycarboxylic acids of the general formula

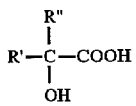

and/or an active amount of one or more α-keto-carboxylic acids of the general formula

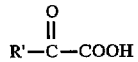

wherein R' and R" independently of one another are chosen from the group consisting of
   (b1) H—,
   (b2) branched or unbranched $C_{1-25}$-alkyl-,
   (b3) branched or unbranched $C_{1-25}$-alkyl- which is substituted by one or more carboxyl groups and/or hydroxyl groups and/or aldehyde groups and/or oxo groups (keto groups),
   (b4) phenyl- and
   (b5) phenyl- which is substituted by one or more carboxyl groups and/or hydroxyl groups and/or branched and/or unbranched $C_{1-25}$-alkyl groups, or wherein the α-carbon atom of the α-hydroxycarboxylic acid, together with R' and R", forms a
   (b6) unsubstituted cycloalkyl group having 3 to 7 ring atoms or a
   (b7) cycloalkyl group having 3 to 7 ring atoms which is substituted by one or more carboxyl groups and/or hydroxyl groups and/or oxo groups (keto groups) and/or branched and/or unbranched $C_{1-25}$-alkyl groups, and where the α-hydroxycarboxylic acid or the α-hydroxycarboxylic acids or the α-keto-carboxylic acid or the α-keto-carboxylic acids can optionally be present in the form of their physiologically tolerated salts and/or ethyl esters and/or methyl esters, and c) an active amount of one or more antioxidants.

2. Active compound combinations according to claim 1, wherein the weight ratio of biotin and/or esters thereof to the α-hydroxycarboxylic acid or acids and/or the α-keto-carboxylic acid or acids is in the range from 1:500 to 20:1.

3. Active compound combinations according to claim 1, wherein the biotin esters are compounds of the structure:

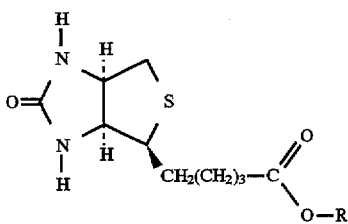

wherein R is H, branched or unbranched $C_{1-18}$-alkyl- or branched or unbranched $C_{1-18}$-alkenyl-.

4. Active compound combinations according to claim 1, wherein the α-hydroxy acids are chosen from the group consisting of (b2) α-hydroxy-fatty acids, (b3) α-hydroxy-sugar acids or aliphatic α-hydroxy-fruit acids, (b4) unsubstituted aromatic α-hydroxycarboxylic acids and (b5) substituted aromatic α-hydroxycarboxylic acids.

5. Active compound combinations according to claim 4, wherein the α-hydroxy acids are chosen from the group consisting of (b2) α-hydroxycarboxylic acids according to the formula

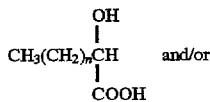

α-hydroxy-isocarboxylic acids according to the formula

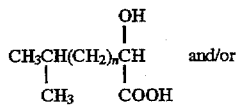

α-hydroxy-anteisocarboxylic acids according to the formula

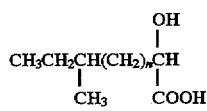

wherein n in each case is a number from 7 to 31, and (b3) aldonic acids, aldaric acids, uronic acids, glyceric acid, malic acid, lactic acid, hydroxy acetic acid and citric acid.

6. Active compound combinations according to claim 1, wherein the antioxidants are chosen from the group consisting of ascorbic acid, ascorbic acid derivatives, tocopherols, tocopheryl esters and other tocopherol derivatives, folic acid, phytic acid, ubiquinones, bile extract, cis-urocanic acid, trans-urocanic acid, carnosine, histidine, flavones, flavonoids, cysteine, cysteine, cysteine derivatives, tyrosine, carotenes and lycopene (psi-carotene), α-liponic acid, glutathione, glutathione esters, zinc oxide and zinc salts. salts.

7. Cosmetic and/or dermatological formulations comprising an active amount of an active compound combination according to claim 1.

8. Cosmetic and/or dermatological formulations according to claim 7, wherein the active amount ranges from 0.001–0.20% by weight of biotin and/or biotin esters, 0.001–5.00% by weight of one or more α-hydroxycarboxylic acids and/or one or more α-keto-carboxylic acids and 0.001–10.00% by weight of an antioxidant or several antioxidants.

9. Process for the preparation of the cosmetic or dermatological formulations according to claim 7, wherein the biotin and/or biotin esters, preferably in an amount corresponding to 0.001–0.20% by weight, one or more α-hydroxycarboxylic acids and/or one or more α-ketocarboxylic acids in an amount corresponding to 0.001–5.0% by weight, and an antioxidant or several antioxidants in an amount corresponding to 0.001–5.00% by weight, in each case based on the total weight of the formulations, are incorporated into cosmetic or dermatological formulations in a known manner.

10. A method of caring for at least one of the skin and an integumentary appendages which comprises applying thereto an amount effective therefor of a combination according to claim 1.

11. A method of improving the appearance of dry skin which comprises applying thereto an amount effective therefor of a combination according to claim 1.

12. A method of improving the appearance of aged skin which comprises applying thereto an amount effective therefor of a combination according to claim 1.

13. A method of stimulating the endogenous capacity for the synthesis of skin fats or biochemical precursors thereof which comprises applying thereto an amount effective therefor of a combination according to claim 1.

14. A method of treating the skin of a patient with the manifestation of a topic dermatitis or seborrhoeic eczema which comprises applying thereto an amount effective therefor of a combination according to claim 1.

15. Active compounds according to claim 6, wherein the cysteine derivative is N-acetylcysteine.

16. Active compounds according to claim 6, wherein the carotene is β-carotene.

* * * * *

UNITED STATES PATENT AND TRADEMARK OFFICE
CERTIFICATE OF CORRECTION

PATENT NO. : 5,710,177
DATED : January 20, 1998
INVENTOR(S) : Sauermann, et al.

It is certified that error appears in the above-indentified patent and that said Letters Patent is hereby corrected as shown below:

Col. 21, line 2     Delete "where" " and substitute -- wherein --

Col. 22, line 11    Delete " salts, " (second occurrence)

Col. 22, line 28    Delete " preferably "

Col. 22, line 31    Delete " 0.001-5.0% " and substitute -- 0.001-5.00% --

Signed and Sealed this

Twenty-fourth Day of November, 1998

Attest:

BRUCE LEHMAN

Attesting Officer        Commissioner of Patents and Trademarks